United States Patent
Mueller et al.

(10) Patent No.: US 9,345,650 B2
(45) Date of Patent: May 24, 2016

(54) COMPOSITION AND METHOD FOR THE SMOOTHING OF FIBRES CONTAINING KERATIN

(75) Inventors: Burkhard Mueller, Hamburg (DE); Meike Ludwig, Hamburg (DE); Inge Neubueser, Hamburg (DE)

(73) Assignee: HENKEL AG & CO. KGAA, Dusseldorf (DE)

(*) Notice: Subject to any disclaimer, the term of this patent is extended or adjusted under 35 U.S.C. 154(b) by 143 days.

(21) Appl. No.: 13/016,180

(22) Filed: Jan. 28, 2011

(65) Prior Publication Data

US 2011/0162670 A1    Jul. 7, 2011

Related U.S. Application Data

(62) Division of application No. 11/574,724, filed as application No. PCT/EP2005/008438 on Aug. 4, 2005, now abandoned.

(30) Foreign Application Priority Data

Sep. 7, 2004  (DE) .......................... 10 2004 043 112

(51) Int. Cl.
    *A61K 8/81*    (2006.01)
    *A61Q 5/06*    (2006.01)
    *A61K 8/41*    (2006.01)
    *A61Q 5/04*    (2006.01)

(52) U.S. Cl.
    CPC .................. *A61K 8/416* (2013.01); *A61K 8/817* (2013.01); *A61K 8/8152* (2013.01); *A61Q 5/04* (2013.01); *A61K 2800/5426* (2013.01); *A61K 2800/596* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 1,985,424 A | 12/1934 | Piggott | |
| 2,016,962 A | 10/1935 | Flint et al. | |
| 2,703,798 A | 3/1955 | Schwartz | |
| 4,744,977 A | 5/1988 | Hensen et al. | |
| 4,834,971 A * | 5/1989 | Klenk et al. | 424/70.4 |
| 4,865,774 A | 9/1989 | Fabry et al. | |
| 4,931,218 A | 6/1990 | Schenker et al. | |
| 5,294,726 A | 3/1994 | Behler et al. | |
| 5,312,932 A | 5/1994 | Behler et al. | |
| 5,322,957 A | 6/1994 | Fabry et al. | |
| 5,484,531 A | 1/1996 | Kuehne et al. | |
| 6,235,913 B1 | 5/2001 | Raths et al. | |
| 7,332,466 B2 | 2/2008 | Schmid et al. | |
| 2003/0206933 A1 | 11/2003 | Schulze zur Wiesche et al. | |
| 2004/0076595 A1 * | 4/2004 | Khan | 424/70.11 |

FOREIGN PATENT DOCUMENTS

| | | |
|---|---|---|
| DE | 10061419 A1 | 6/2002 |
| DE | 10061420 * | 6/2002 |
| EP | 0690044 B1 | 1/1996 |
| EP | 0814767 B1 | 1/1998 |
| WO | 9206984 A1 | 4/1992 |
| WO | 9725964 A1 | 7/1997 |
| WO | 0245666 A2 | 6/2002 |
| WO | 2004032887 A1 | 4/2004 |

OTHER PUBLICATIONS

McMullen, R. et al. "Thermal degradation of hair. I. Effect of curling irons." Journal of Cosmetic Science, vol. 49, Jul./Aug. 1998, pp. 223-244.
Biswas, A.K. et al., "Surface-Active Properties of Sodium Salts of Sulfated Fatty Acid Monoglycerides." The Journal of the American Oil Chemists' Society, vol. 37, 1960, pp. 171-175.
Ahmed, Fahim U. "Efficient Synthesis of Fatty Monoglyceride Sulfates from Fatty Acids and Fatty Acid Methyl Esters." J. Am. Oil. Chem. Soc., vol. 67I, No. 1, Jan. 1990, pp. 8-14.
Biermann et al. "Alkyl Polyglucosides—Technology and Properties." Starch, vol. 45, No. 8, 1993, pp. 281-288.
Salka, Barry. "Alkyl Polyglycosides: Properties and Applications." Cosmetics & Toiletries, vol. 108, Mar. 1993, pp. 89-94.
Kahre, J. et al. "Alkyl Polyglycocides—A Novel Concept for Care and Compatibility in Cosmetics." SOFW-Journal, vol. 121, Aug. 1995, p. 598-611.
Heike Kelkenberg, Marl, Detergents Based on Sugar: New Components for Washing Raw Materials and Cosmetics. Tenside Surfactants, Detergents 25, No. 1, 1988, pp. 8-13.
Dörfler, H.D. Grenzflachen-und Kolloidchemie, VCH Verlagsgesellschaft, mbH, 1994.
Römp-Lexikon. Chemie. George Thieme Verlag, vol. 10, 1997, pp. 1764.
Berthiaume, M.D. "Silicones in Hair Care." Society of Cosmetic Chemists Monograph Series, 1997, pp. 11-25.

* cited by examiner

*Primary Examiner* — Tigabu Kassa
(74) *Attorney, Agent, or Firm* — Ingrassia Fisher & Lorenz, P.C.

(57) ABSTRACT

The invention relates to a composition which is oxidatively effective on keratin-containing fibers, in particular human hair, and which, besides at least one oxidizing agent, comprises an active ingredient combination of (a) a selected cationic polymer, (b) at least one mono- or di(C.sub.8- to C.sub.30)-alkylammonium salt and (c) at least one quaternary ammonium compound which carries at least one selected group on the quaternized nitrogen atom, and to a method of reshaping keratin-containing fibers, in which this composition is used, and to the use of this composition for fixing in the course of hair reshaping. The reshaping is improved through these compositions and the fiber receives excellent care and structure retention.

16 Claims, No Drawings

COMPOSITION AND METHOD FOR THE SMOOTHING OF FIBRES CONTAINING KERATIN

CROSS REFERENCE TO RELATED APPLICATIONS

The present application is a divisional application of U.S. application Ser. No. 11/574,724 filed 5 Mar. 2007 now abandoned, which is a national stage application under 35 U.S.C. §371 of International Patent Application No. PCT/EP05/08438 filed 4 Aug. 2005, which claims priority to German Patent Application No. 10 2004 043 112.4 filed 7 Sep. 2004, each of which are incorporated herein by reference.

The invention relates to a composition which is oxidatively effective on keratin-containing fibers, in particular human hair, and which, besides at least one oxidizing agent, comprises an active ingredient combination of the components
(a) a selected cationic polymer,
(b) at least one mono- or di($C_8$-$C_{30}$)-alkylammonium salt and
(c) at least one quaternary ammonium compound which carries at least one selected group on the quaternized nitrogen atom,
and to a method of reshaping keratin-containing fibers, in which this composition is used, and to the use of this composition for fixing in the course of hair reshaping.

Keratin-containing fibers which may be used are in principle all animal hairs, e.g. wool, horse hair, angora hair, furs, feathers and products or textiles produced therefrom. However, the invention is preferably used in the course of hair reshaping, in particular smoothing frizzy human hair and wigs produced therefrom.

A permanent shaping of keratin-containing fibers is usually carried out by mechanically shaping the fibers and fixing the shaping using suitable aids. Before and/or after this shaping, the fibers are treated with a keratin-reducing preparation. Following a rinsing operation, the fiber is then treated in a so-called fixing step with an oxidizing agent preparation, rinsed and freed from the shaping aids (rollers, curlers) after or during the fixing step. If the keratin-reducing component used is a mercaptan, e.g., ammonium thioglycolate, this cleaves some of the disulfide bridges of the keratin molecule to —SH groups, resulting in a softening of the keratin fibers. Upon subsequent oxidative fixing, disulfide bridges become linked again within the hair keratin, meaning that the keratin structure is fixed in the pregiven shape. Alternatively, it is known to use sulfite instead of mercaptans for shaping hair. By means of hydrogen sulfite solutions and/or sulfite solutions and/or disulfite solutions, disulfide bridges in the keratin are cleaved in a sulfitolysis in accordance with the equation

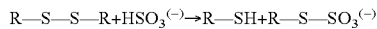

and in this way softening of the keratin fibers is achieved. Reducing agents which contain hydrogen sulfite, sulfite or disulfite do not have the strong intrinsic odor of compositions which comprise mercaptan. As described above, the cleavage can be reversed again in a fixing step with the help of an oxidizing agent with the formation of new disulfide bridges.

The permanent smoothing of keratin-containing fibers is achieved analogously through the use of keratin-reducing and keratin-oxidizing compositions. In a corresponding method, the frizzy hair is either wound onto rollers with a large diameter of usually more than 15 mm, or the hair is combed smooth under the action of the keratin-reducing composition. Instead of the roller, it is also possible to smooth the fibers on a smoothing board. Smoothing boards are usually rectangular panels, e.g., made of plastic. The fiber is preferably wetted here with the keratin-reducing preparation.

Another way of smoothing hair is smoothing using a hot iron. However, the structure of the keratin-containing fiber changes while heat-treating the hair during smoothing (see for this R. McMullen et al., *J. Cosmet. Sci.*, 1998, Vol. 49, pp. 223-244). This change in the fiber structure should be countered by suitable measures.

In general, known reshaping methods, particularly during smoothing, have the disadvantage that the keratin-containing fiber becomes electrostatically charged. Moreover, the reshaping result of the known methods with regard to the degree of reshaping and uniformity of the reshaping is in need of improvement. If an improvement in the degree of reshaping is achieved, this is in most cases accompanied by increased damage to the keratin-containing fibers.

An object of the invention is therefore to provide a reshaping method for keratin-containing fibers, in particular for human hair, which produces an improved reshaping result, cares for the fibers and protects the structure of the fibers.

The printed specification WO-A1-97/25964 discloses leave-on compositions for conditioning keratin-containing fibers which comprise cationic polymers, in particular polyquaternium-37. The use of these polymers in the combination according to the invention with two further special cationic compounds is not mentioned.

The printed specifications EP-A1-1 339 379 and EP-A1-1 280 496 disclose compositions containing hydrogen peroxide and polyquaternium-37.

The printed specification EP-A1-814 767 discloses the combination of a quaternary dialkylammonium salt with at least one ester bond and a further cationic surfactant as conditioning composition for keratin-containing fibers.

Surprisingly, it has been found that the object is achieved by the composition according to the invention described in more detail below. This composition serves as a fixing composition in a method for reshaping keratin-containing fibers, in particular human hair.

The invention firstly provides a composition comprising, besides at least one oxidizing agent, an active ingredient combination of the components
(a) a cationic polymer which has at least one structural element of the general formula (I),

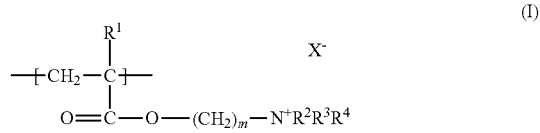

in which
$R^1$ is a hydrogen atom or a ($C_1$-$C_4$)-alkyl group,
$R^2$, $R^3$ and $R^4$, independently of one another, are ($C_1$-$C_4$)-alkyl groups, ($C_2$-$C_4$)-alkenyl groups or ($C_2$-$C_4$)-hydroxyalkyl groups,
m is a number 1, 2, 3 or 4 and
$X^-$ is a physiologically compatible organic or inorganic anion,
(b) at least one quaternary ammonium compound of the formula (II)

where
$R^5$ is a linear or branched ($C_8$-$C_{30}$)-alkyl group,
y is 1 or 2, and Y⁻ is a physiologically compatible organic or inorganic anion, and (c) at least one quaternary ammonium compound which comprises at least one group of the formula (III),

  (III)

where

R⁶ is a saturated or unsaturated, linear or branched, optionally substituted $(C_8\text{-}C_{30})$-hydrocarbon group, A¹ is a carbonyl group or a direct bond, A² is a direct bond, NH or an oxygen atom, and A³ is a $(C_2\text{-}C_4)$-alkylene group or a $(C_2\text{-}C_4)$-hydroxyalkylene group, with the provisos that A³ bonds to the quaternary nitrogen atom of the quaternary ammonium compound and A³ is a $(C_2\text{-}C_4)$-hydroxyalkylene group when A¹ and A² are a direct bond.

The following examples of substituents of the abovementioned formulae are to be applied to the formulae (I) (II), (III), (c1) and (c2):

Examples of a $(C_1\text{-}C_4)$-alkyl group are methyl, ethyl, propyl, isopropyl, n-butyl, sec-butyl and tert-butyl.

Examples of a $(C_8\text{-}C_{30})$-alkyl group are n-octyl, n-decyl, n-dodecyl, n-tetradecyl, n-hexadecyl, stearyl, isostearyl and eicosyl.

Examples of a $(C_1\text{-}C_{30})$-alkyl group are the abovementioned examples of the particular alkyl groups and also n-pentyl, an isopentyl, n-hexyl and an n-heptyl group.

Examples of a $(C_2\text{-}C_4)$-alkenyl group are vinyl, allyl and butenyl.

Examples of a $(C_2\text{-}C_4)$-hydroxyalkyl group are a 2-hydroxyethyl group, a 2-hydroxypropyl group, a 3-hydroxypropyl group and a 4-hydroxybutyl group.

Examples of a $(C_2\text{-}C_4)$-alkylene group is ethylene, propane-1,2-diyl, propane-1,3-diyl, and butane-1,4-diyl.

Examples of a $(C_2\text{-}C_4)$-hydroxyalkylene group is 2-hydroxyethylene, 1-hydroxypropane-1,2-diyl, 1-hydroxypropane-1,3-diyl and 2-hydroxypropane-1,3-diyl.

The oxidizing agent present in the composition according to the invention has a redox potential such that two mercapto groups can be oxidized with formation of a disulfide bridge. A preferred oxidizing agent is chosen from, for example, sodium bromate, potassium bromate or hydrogen peroxide. It is particularly preferred to use hydrogen peroxide as oxidizing agent. To stabilize aqueous hydrogen peroxide preparations, customary stabilizers can additionally be added. The pH of the aqueous $H_2O_2$ preparations, which usually comprise about 0.5 to 3.0% by weight of $H_2O_2$, is preferably 2 to 6. If the composition according to the invention comprises bromate as oxidizing agent, then this is usually present in concentrations of from 1 to 10% by weight and the pH of the solutions is adjusted to 4 to 7.

According to the invention, preference is given to those cationic polymers with at least one structural unit according to formula (I) for which at least one of the following conditions is true:

R¹ is a methyl group,

R², R³ and R⁴ are methyl groups, m has the value 2.

Suitable physiologically compatible organic or inorganic counterions X⁻ according to formula (I) are, for example, halide ions, sulfate ions, phosphate ions, methosulfate ions and organic ions, such as lactate, citrate, tartrate and acetate ions. Preference is given to halide ions, in particular chloride.

If the cationic polymer present in the compositions according to the invention is present as a copolymer, then these consist essentially of the structural elements described in formula (I), and of nonionogenic comonomer units. Copolymers with structural elements according to formula (I) comprise, as nonionogenic monomer units, preferably acrylamide, methacrylamide, acrylic $C_{1\text{-}4}$-alkyl esters and methacrylic $C_{1\text{-}4}$-alkyl esters. Among these nonionogenic monomers, acrylamide is particularly preferred. These copolymers can also be crosslinked, as described below in the case of the homopolymers. A copolymer preferred according to the invention is the crosslinked acrylamide/methacryloyloxyethyltrimethylammonium chloride copolymer. Such copolymers in which the monomers are present in a weight ratio of about 20:80 are available commercially as about 50% strength nonaqueous polymer dispersion under the name Salcare® SC 92.

Homopolymers of one structural element according to formula (I) are particularly preferred cationic polymers.

A particularly preferred cationic polymer is the, if desired crosslinked, poly(methacryloyloxyethyltrimethylammonium chloride with the INCI name Polyquaternium-37. The crosslinking can take place, if desired, using polyolefinically unsaturated compounds, for example divinylbenzene, tetraallyloxyethane, methylenebisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylenebisacrylamide is a preferred crosslinking agent. The homopolymer is preferably used in the form of a nonaqueous polymer dispersion, which should have a polymer fraction not below 30% by weight. Such polymer dispersions are available commercially under the names Salcare® SC 95 (about 50% polymer fraction, further components: mineral oil (INCI name: Mineral Oil) and tridecyl polyoxypropylene polyoxyethylene ether (INCI name: PPG-1 trideceth-6)) and Rheocare® CTH (E) and Salcare® SC 96 (about 50% polymer fraction, further components: mixture of diesters of propylene glycol with a mixture of caprylic acid and capric acid (INCI name: Propylene Glycol Dicaprylate/Dicaprate) and tridecyl polyoxypropylene polyoxyethylene ether (INCI name: PPG-1 trideceth-6)).

Compositions according to the invention comprise the cationic polymer with at least one structural element of the formula (I) preferably in an amount of from 0.01 to 10% by weight, particularly preferably from 0.1 to 5% by weight, in each case based on the weight of the composition.

For component (b) of the composition according to the invention, the radical R⁵ of the formula (II) is preferably an alkyl group having 10 to 22 carbon atoms, particularly preferably having 10 to 18 carbon atoms.

Quaternary ammonium compounds of the formula (II) present in the compositions according to the invention as component (b) are preferably halides, in particular chlorides and bromides.

Preferred compounds of the formula (II) are salts, in particular halides, of dicetyldimethylammonium, distearyldimethylammonium (e.g. dioctadecyldimethylammonium chloride as Genamin® DSAc from Clariant), cetyltrimethylammonium (e.g., hexadecyltrimethylammonium chloride as Dehyquart® A from Cognis), or of stearyltrimethylammonium.

Quaternary ammonium compounds (c) comprise saturated or unsaturated, linear or branched, optionally substituted ($C_8$- to $C_{30}$)-hydrocarbon groups. These are understood firstly as meaning hydrocarbon groups which comprise 8 to 30 carbon atoms which form a linear or branched, saturated or unsaturated carbon backbone. This carbon backbone is not interrupted by heteroatoms. Heteroatoms are atoms which differ from carbon and hydrogen, in particular nitrogen, oxygen and sulfur. According to the invention, these include those hydrocarbon groups which carry heteroatom-containing groups as substituents for hydrogen atoms. According to the invention, it is preferred that the saturated or unsaturated, linear or branched ($C_8$ to $C_{30}$)-hydrocarbon groups carry 0 to 4 such heteroatom-containing groups, in particular 0 to 2, particularly 1 or 0.

Preferred saturated or unsaturated, linear or branched ($C_8$ to $C_{30}$)-hydrocarbon groups according to the invention are linear or branched ($C_8$-$C_{30}$)-alkyl groups (examples of these have been defined above), linear or branched ($C_8$-$C_{30}$)-alkenyl groups (for example 9-octadecen-1-yl, 9,12-octadecadien-1-yl, 9,12,15-octadecatrien-1-yl, 13-docosen-1-yl), hydroxy-($C_8$-$C_{30}$)-alkyl groups (for example 2-hydroxydecyl, 2-hydroxydodecyl, 2-hydroxytetradecyl, 2-hydroxyhexadecyl and 2-hydroxyoctadecyl) and oligohydroxy-($C_8$-$C_{30}$)-alkyl groups with preferably 2 to 4 hydroxyl groups.

When selecting the compounds (c) it is preferred if the group according to formula (III) is chosen from
an ω-[($C_8$- to $C_{30}$)-alkanoyloxy]-($C_2$- to $C_4$)-alkyl group, ($R^6$=($C_8$- to $C_{30}$)-alkyl, $A^1$=carbonyl, $A^2$=oxygen atom, $A^3$=($C_2$- to $C_4$)-alkylene group),
an ω-[($C_8$- to $C_{30}$)-alkylamido]-($C_2$- to $C_4$)-alkyl group ($R^6$=($C_8$- to $C_{30}$)-alkyl, $A^1$=carbonyl, $A^2$=group NH, $A^3$=($C_2$- to $C_4$)-alkylene group),
a ($C_{10}$- to $C_{34}$)-hydroxyalkyl group (either: $R^6$=($C_8$- to $C_{30}$)-alkyl, $A^1$=direct bond, $A^2$=direct bond, $A^3$=($C_2$- to $C_4$)-hydroxyalkylene group or: $R^6$=($C_8$- to $C_{30}$)-hydroxyalkyl or oligohydroxy-($C_8$- to $C_{30}$)-alkyl group, $A^1$=direct bond, $A^2$=direct bond, $A^3$=($C_2$- to $C_4$)-alkylene group.

Examples of ω-[($C_8$- to $C_{30}$)-alkanoyloxy]-($C_2$- to $C_4$)-alkyl groups are the preferred 2-[($C_8$- to $C_{30}$)-acyloxy]ethyl groups, in particular 2-(dodecanoyloxy)ethyl, 2-(tetradecanoyloxy)ethyl, 2-(hexadecanoyloxy)ethyl and 2-(octadecanoyloxy)ethyl.

Preferably, the quaternary ammonium compounds (c) present in the composition according to the invention are those selected from the group consisting of components (c) with one and two groups of the formula (III).

According to the invention, it is preferred that the quaternary ammonium compounds (c) are present in the composition according to the invention in an amount of from 0.05 to 5% by weight, based on the total composition.

The quaternary ammonium compounds (c) comprising precisely one group of the abovementioned formula (III) are preferably chosen from compounds of the formula (c1)

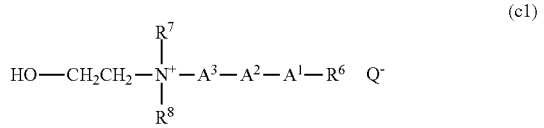

(c1)

in which
$R^7$ and $R^8$, independently of one another, are a hydrogen atom, a ($C_2$- to $C_{30}$)-acyl group or a linear or branched ($C_1$- to $C_{30}$)-alkyl group,
$R^6$ is a linear or branched ($C_8$- to $C_{30}$)-alkyl group or a linear or branched ($C_8$- to $C_{30}$)-alkenyl group,
$A^1$ is a direct bond or a carbonyl group,
$A^2$ is a direct bond, a group NH or an oxygen atom,
$A^3$ is a ($C_2$-$C_4$)-alkylene group or a ($C_2$-$C_4$)-hydroxyalkylene group, and $Q^-$ is a physiologically compatible organic or inorganic anion,
with the proviso that $A^3$ is a ($C_2$-$C_4$)-hydroxyalkylene group if $A^1$ and $A^2$ are a direct bond.

Suitable physiologically compatible organic or inorganic counterions $Q^-$ according to formula (c1) are, for example, halide ions, sufate ions, phosphate ions, methosulfate ions, and organic ions, such as lactate, citrate, tartrate and acetate ions. Preference is given to methosulfate and halide ions, in particular chloride.

According to the invention, preference is given to those compounds according to formula (c1) for which at least one of the following conditions is true:
$A^1$ is a carbonyl group if $A^2$ is an oxygen atom or a group NH.
$R^7$ and $R^8$ are a ($C_1$- to $C_4$)-alkyl group, in particular a methyl group.

The examples of radicals according to formula (c1) as were specified for the respective radicals and groups of formulae (I), (II), and (III) are applicable.

Examples of a ($C_1$- to $C_4$)-alkylene group are methylene, ethylene, propane-1,2-diyl, propane-1,3-diyl and butane-1,4-diyl.

Examples of ($C_8$- to $C_{30}$)-acyl groups are octanoyl, decanoyl, dodecanoyl, tetradecanoyl, hexadecanoyl, octadecanoyl and eicosanoyl.

Quaternary ammonium compounds (c) comprising two groups of the abovementioned formula (III) are generally preferably chosen from compounds with the formula (c2)

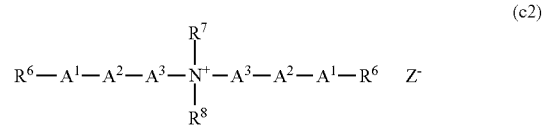

(c2)

in which
$R^7$ and $R^8$, independently of one another, are a hydrogen atom, a ($C_1$- to $C_4$)-alkyl group or a ($C_2$- to $C_4$)-hydroxyalkyl group,
$R^6$ is a linear or branched ($C_8$- to $C_{30}$)-alkyl group, linear or branched ($C_8$- to $C_{30}$)-alkenyl group, a hydroxy-($C_8$- to $C_{30}$)-alkyl group or an oligohydroxy-($C_8$- to $C_{30}$)-alkyl group
$A^1$ is a carbonyl group,
$A^2$ is a group NH or an oxygen atom,
$A^3$ is a ($C_2$-$C_4$)-alkylene group or a ($C_2$-$C_4$)-hydroxyalkylene group, and
$Z^-$ is a physiologically compatible organic or inorganic anion.

Examples of the radicals according to formula (c2) as were specified for the respective radicals and groups of the formulae (I), (II), (III) and (c1) are applicable.

According to the invention, preference is given to those compounds according to formula (c2) for which at least one of the following conditions is true:
$R^7$ and $R^8$, independently of one another, are a hydrogen atom, a methyl group or a 2-hydroxyethyl group.
If $R^7$ and $R^8$ are identical, they are preferably a ($C_1$- to $C_4$)-alkyl group, particularly preferably a methyl group.
It is preferred that $A^3$ is chosen from ethylene, propane-1,3-diyl, propane-1,2-diyl, 2-hydroxypropane-1,3-diyl.

Suitable physiologically compatible organic or inorganic counterions $Z^-$ according to formula (c2) are, for example, halide ions, sulfate ions, phosphate ions, methosulfate ions, and organic ions, such as lactate, citrate, tartrate and acetate ions. Preference is given to methosulfate and halide ions, in particular chloride.

The compounds of component (c) according to the invention are preferably selected from the group which is formed from quaternized ester salts of fatty acids with triethanolamine, so-called ester quats, in particular the salts of N,N-di(2-(dodecanoyloxy)ethyl)dimethylammonium, N,N-di(2-(tetradecanoyloxy)ethyl)dimethylammonium, N,N-di(2-(hexadeca-noyloxy)ethyl)dimethylammonium, N,N-di(2-(hexadecanoyloxy)propyl)dimethylammonium, N,N-di(2-(octadecanoyloxy)ethyl)dimethylammonium with a physiologically compatible organic or inorganic anion. Preferred anions are alkylsulfates, such as, for example, methylsulfate, and halides, such as chloride and bromide. Such products are sold, for example, under the trade names Stepantex®, Dehyquart® and Armocare®. The products Armocare® VGH-70, a N,N-di(2-hexadecanoyloxyethyl)-dimethylammonium chloride, and Dehyquart® L80 (INCI name: Dicocoylethyl Hydroxyethylmonium Methosulfate), Dehyquart® F-75, Dehyquart® C-4046 and Dehyquart® AU-35 are examples of such ester quats. For the preparation it is also possible to use fatty acid cuts, e.g. tallow fatty acids obtained from tallow such as, for example, beef tallow (INCI names: Ditallowoylethyl Dimonium Methosulfate, Ditallowoyl PG-dimonium Chloride).

salts of N,N-dimethyl-N-(2-hydroxyethyl)-N-(2-hydroxyhexadecyl)ammonium. Preferred halides are chloride and bromide. These are sold, for example, under the trade name Dehyquart® E (INCI name: Aqua (Water), Hydroxycetyl Hydroxyethyl Dimonium Chlorie) by Cognis.

quaternized amide salts of fatty acids with diamines, such as, for example, salts of N-(13-docosen)amidopropyl-N-2-hydroxyethyl-N,N-dimethylammonium (INCI name: Hydroxyethyl Erucamidopropyl Dimonium Chloride) or of N-docosylamidopropyl-N-2-hydroxyethyl-N,N-dimethylammonium, which is sold under the trade name Incroquat® Behenyl HE (INCI name: Hydroxyethyl Behenamidopropyl Dimonium Chloride) by Croda Inc.

The cationic polymers (a) and the quaternized ammonium compounds (b) are preferably used in the compositions according to the invention in a quantitative ratio range of quantity of (a) to quantity of (b) of 0.2:1 to 5:1, particularly preferably in the range from 1:1 to 3:1.

The cationic polymers (a) and the quaternized ammonium compounds (c) are preferably used in the compositions according to the invention in a quantitative ratio range of quantity of (a) to quantity of (c) of 0.2:1 to 5:1, particularly preferably in the range from 1:1 to 3:1.

Compositions according to the invention can additionally comprise silicones. Silicones which can be used according to the invention are preferably linear, cyclic or branched silicones chosen from the types of cyclomethicones, dimethiconoles, dimethicone copolyols, amodimethicones, trimethylsilylamodimethicones and phenyltrimethicones. These silicone types are known to the person skilled in the art under the nomenclature of the Cosmetic, Toiletry and Fragrance Association (CTFA) and are disclosed in: M. D. Berthiaume, *Society of the Cosmetic Chemists Monograph Series*, "Silicones in Hair Care", Ed.: L. D. Rhein, publisher: Society of the Cosmetic Chemists, 1997, Chapter 2, to which reference is explicitly made at this point. Polysiloxanes, such as dialkyl- and alkylarylsiloxanes, for example dimethylpolysiloxane and methylphenylpolysiloxane, and alkoxylated analogs thereof, analogs terminated with hydroxyl groups and quaternized analogs, and cyclic siloxanes. Here, the silicones with the INCI names Dimethicone, PEG-12 Dimethicone, PEG/PPG-18/18 Dimethicone, Cyclomethicone, Dimethiconol, Quarternium-80 and Amodimethicone, and mixtures thereof are particularly preferred silicones.

Examples of such silicones are products sold by Dow Corning under the names DC 190 (INCI name: PEG/PPG-18/18 Dimethicone), DC 193 (INCI name: PEG-12 Dimethicone), DC 200, DC 1401 (INCI name: Cyclomethicone, Dimethiconol) and DC 1403 (INCI name: Dimethicone, Dimethiconol), and the commercial products DC 244 (INCI name: Cyclomethicone), DC 344 (INCI name: Cyclomethicone) and DC 345 (INCI name: Cyclomethicone) from Dow Corning, Q2-7224 (manufacturer: Dow Corning; a stabilized trimethylsilylamodimethicone, Dow Corning 929 emulsion (comprising a hydroxyamino-modified silicone, which is also referred to as amodimethicone), SM-2059 (manufacturer: General Electric), SLM-55067 (manufacturer: Wacker), and Abil Quat 3270 and 3272 (manufacturer: Th. Goldschmidt; diquaternary polydimethylsiloxanes, INCI name: Quaternium-80).

The silicones are preferably present in amounts of from 0.1 to 10% by weight, particularly preferably from 0.3 to 5% by weight, in each case based on the weight of the composition.

Compositions according to the invention can additionally comprise protein-hydrolyzates. Protein hydrolyzates are product mixtures which are obtained by acidically, basically or enzymatically catalyzed degradation of proteins. According to the invention, protein hydrolyzates of both vegetable and animal origin can be used.

Animal protein hydrolyzates are, for example, the protein hydrolyzates of elastin, collagen, keratin, silk and milk protein, which can also be in the form of salts. Such products are sold, for example, under the trade names Dehylan® (Cognis), Promois® (RITA Corp.), Collapuron® (Cognis), Nutrilan® (Cognis), Gelita-Sol® (Deutsche Gelatine Fabriken Stoess & Co.), Lexein® (Inolex) and Kerasol® (Croda).

A preferred protein hydrolyzate is the silk protein hydrolyzate (Promois® Silk 720, Promois® Silk 1000).

The use of protein hydrolyzates of vegetable origin, e.g. soya, almond, rice, pea, potato and wheat protein hydrolyzates, is likewise in accordance with the invention. Such products are obtainable, for example, under the trade marks Gluadin® (Cognis), DiaMin® (Diamalt), Lexein® (Inolex) and Crotein® (Croda).

Likewise possible is the use of derivatives of the protein hydrolyzates, for example in the form of their fatty acid condensation products. Such products are sold, for example, under the names Lamepon® (Cognis), Gluadin® (Cognis), Lexein® (Inolex), Crolastin® (Croda) or Crotein® (Croda).

Although the use of the protein hydrolyzates is preferred as such, instead of them it is in some cases also possible to use amino acid mixtures obtained in other ways or individual amino acids and amino acid derivatives, such as, for example, arginine, asparagines, aspartic acid, citrullin, histidine, ornithine, lysine and pyrroglutamic acid. The amino acids can be used either as free amino acids, or as salts, e.g. as hydrochlorides or alkali metal, alkaline earth metal or ammonium salts. In addition, oligopeptides of, on average, 2-3 amino acids which have a high fraction (>50%, in particular >70%) of the specified amino acids have also proven useful according to the invention.

According to the invention, particular preference is given to arginine, asparagines, aspartic acid and their salts and oligopeptides and hydrolyzates which are rich in the specified preferred amino acids. Very particular preference is given to asparagines and aspartic acid, and to the salts and hydrolyzates thereof.

In addition, the compositions according to the invention can comprise at least one surface-active substance from the group of anionic, amphoteric, zwitterionic and nonionic surfactants. The surfactants have the task, inter alia, of promoting the wetting of the keratin surface by the treatment solution.

Suitable anionic surfactants in preparations according to the invention are in principle all anionic surface-active substances suitable for use on the human body. These are characterized by a solubilizing anionic group, such as, for example, a carboxylate, sulfate, sulfonate or phosphate group, and a lipophilic alkyl group with about 8 to 30 carbon atoms. Additionally, glycol or polyglycol ether groups, ester groups, ether groups and amide groups and also hydroxyl groups may be present in the molecule. Examples of suitable anionic surfactants are, in each case in the form of the sodium, potassium and ammonium and also the mono-, di- and trialkanolammonium salts having 2 to 4 carbon atoms in the alkanol group, linear and branched fatty acids having 8 to 30 carbon atoms (soaps), ether carboxylic acids of the formula R—O—(CH$_2$—CH$_2$O)$_x$—CH$_2$—COOH, in which R is a linear alkyl group having 8 to 30 carbon atoms and x=0 or 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic mono- and dialkyl esters having 8 to 24 carbon atoms in the alkyl group and sulfosuccinic monoalkyl polyoxyethyl esters having 8 to 24 carbon atoms in the alkyl group and 1 to 6 oxyethyl groups, linear alkanesulfonates having 8 to 24 carbon atoms, linear alpha-olefinsulfonates having 8 to 24 carbon atoms, alpha-sulfo fatty acid methyl esters of fatty acids having 8 to 30 carbon atoms, alkyl sulfates and alkylpolyglycol ether sulfates of the formula R—O(CH$_2$—CH$_2$O)$_x$—OSO$_3$H, in which R is a preferably linear alkyl group having 8 to 30 carbon atoms and x=0 or 1 to 12, mixtures of surface-active hydroxysulfonates as in DE-A-37 25 030, sulfated hydroxyalkyl polyethylene and/or hydroxyalkylene propylene glycol ethers as in DE-A-37 23 354, sulfonates of unsaturated fatty acids having 8 to 24 carbon atoms and 1 to 6 double bonds as in DE-A-39 26 344, esters of tartaric acid and citric acid with alcohols, which constitute addition products of about 2-15 molecules of ethylene oxide and/or propylene oxide onto fatty alcohols having 8 to 22 carbon atoms, alkyl and/or alkenyl ether phosphates of the formula (E1-I),

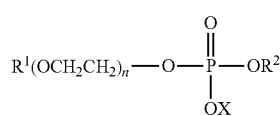

(E1-I)

in which R$^1$ is preferably an aliphatic hydrocarbon radical having 8 to 30 carbon atoms, R$^2$ is hydrogen, a radical (CH$_2$CH$_2$O)$_n$R$^1$ or X, n is numbers from 1 to 10 and X is hydrogen, an alkali metal or alkaline earth metal or NR$^3$R$^4$R$^5$R$^6$, where R$^3$ to R$^6$, independently of one another, are hydrogen or a C1 to C4-hydrocarbon radical, sulfated fatty acid alkylene glycol esters of the formula (E1-II)

in which R$^7$CO— is a linear or branched, aliphatic, saturated and/or unsaturated acyl radical having 6 to 22 carbon atoms, Alk is CH$_2$CH$_2$, CHCH$_3$CH$_2$ and/or CH$_2$CHCH$_3$, n is numbers from 0.5 to 5 and M is a cation, as described in DE-A-197 36 906.5, monoglyceride sulfates and monoglyceride ether sulfates of the formula (E1-III)

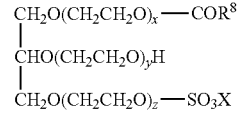

(E1-III)

in which R$^8$CO is a linear or branched acyl radical having 6 to 22 carbon atoms, x, y and z are in total 0 or numbers from 1 to 30, preferably 2 to 10, and X is an alkali metal or alkaline earth metal. Typical examples of monoglyceride (ether) sulfate suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and ethylene oxide adducts thereof with sulfur trioxide or chlorosulfonic acid in the form of its sodium salts. Preference is given to using monoglyceride sulfates of the formula (E1-III) in which R.sup.8CO is a linear acyl radical having 8 to 18 carbon atoms, as have been described, for example, in EP-B 1 0 561 825, EP-B1 0 561 999, DE-A1 42 04 700 or by A. K. Biswas et al. in J. Am. Oil. Chem. Soc., Vol. 37, 171 (1960) and F. U. Ahmed in J. Am. Oil. Chem. Soc., Vol. 67, 8 (1990), amide ether carboxylic acids, as described in EP 0 690 044, condensation products of C$_8$-C$_{30}$-fatty alcohols with protein hydrolyzates and/or amino acids and derivatives thereof, which are known to the person skilled in the art as protein fatty acid condensates, such as, for example, the Lamepon® grades, Gluadin® grades, Hostapon® KCG or the Amisoft® grades.

Preferred anionic surfactants are alkylsulfates, alkyl polyglycol ether sulfates and ether carboxylic acids having 10 to 18 carbon atoms in the alkyl group and up to 12 glycol ether groups in the molecule, sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups, monoglyceride sulfates, alkyl and alkenyl ether phosphates, and protein fatty acid condensates.

Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethylammonium glycinates, for example cocoalkyl dimethylammonium glycinate, N-acylaminopropyl-N,N-dimethylammonium glycinates, for example cocoacyl aminopropyldimethylammonium glycinate, and 2-alkyl-3-carboxymethyl-3-hydroxyethylimidazolines having in each case 8 to 18 carbon atoms in the alkyl or acyl group, and cocoacyl aminoethyl hydroxyethylcarboxymethyl glycinate. A preferred zwitterionic surfactant is the fatty acid amide derivative known under the INCI name Cocoamidopropyl Betaine.

Ampholytic surfactants are understood as meaning those surface-active compounds which, apart from a $C_8$-$C_{24}$-alkyl or -acyl group in the molecule, comprise at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Particularly preferred ampholytic surfactants are N-cocoalkylaminopropionate, cocoacylaminoethylaminopropionate and $C_{12}$-$C_{18}$-acylsarcosine.

Nonionic surfactants comprise, as hydrophilic group, e.g., a polyol group, a polyalkylene glycol ether group or a combination of polyol and polyglycol ether group. Such compounds are, for example,

- addition products of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group,
- addition products, terminally capped with a methyl or $C_2$-$C_6$ alkyl radical, of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, such as, for example, the grades obtainable under the trade names Dehydol® LS, Dehydol® LT (Cognis),
- $C_{12}$-$C_{30}$-fatty acid mono- and diesters of addition products of from 1 to 30 mol of ethylene oxide onto glycerol,
- addition products of from 5 to 60 mol of ethylene oxide onto castor oil and hydrogenated castor oil,
- polyol fatty acid esters, such as, for example, the commercial product Hydagen® HSP (Cognis) or Sovermol grades (Cognis),
- alkoxylated triglycerides,
- alkoxylated fatty acid alkyl esters of the formula (E4-I)

$$R^1CO\text{—}(OCH_2CHR^2)_w OR^3 \qquad \text{(E4-I)}$$

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms, and w is numbers from 1 to 20,
- amine oxides,
- hydroxyl mixed ethers, as are described, for example, in DE-A 19738866,
- sorbitan fatty acid esters and addition products of ethylene oxide onto sorbitan fatty acid esters, such as, for example, the polysorbates,
- sugar fatty acid esters and addition products of ethylene oxide onto sugar fatty acid esters,
- addition products of ethylene oxide onto fatty acid alkanolamides and fatty amines,
- sugar surfactants of the alkyl and alkenyl oligoglycoside type according to formula (E4-II), $$R^4O\text{-}[G]_p \qquad \text{(E4-II)}$$

in which $R^4$ is an alkyl or alkenyl radical having 4 to 22 carbon atoms, G is a sugar radical having 5 or 6 carbon atoms and p is numbers from 1 to 10. They can be obtained by the relevant methods of preparative organic chemistry. As a representative of the extensive literature, reference may be made here to the overview paper by Biermann et al. in Starch/Stärke, Vol. 45, 281 (1993), B. Salka in Cosm. Toil., Vol. 108, 89 (1993) and J. Kahre et al. in SÖFW-Journal, Vol. 8, 598 (1995).

The alkyl and alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (E4-II) gives the degree of oligomerization (DP), i.e., the distribution of monoglycosides and oligoglycosides and is a number between 1 and 10. While p in the individual molecule must always be an integer and here can primarily assume the values p=1 to 6, the value p for a specific alkyl oligoglycoside is an analytically determined calculated value, which in most cases is a fraction. Preferably, alkyl and/or alkenyl oligoglycosides with an average degree of oligomerization p of from 1.1 to 3.0 are used. From the point of view of application, preference is given to those alkyl and/or alkenyl oligoglycosides whose degree of oligomerization is less than 1.7 and is in particular between 1.2 and 1.4. The alkyl or alkenyl radical $R^4$ can be derived from primary alcohols having 4 to 11, preferably 8 to 10, carbon atoms. Typical examples are butanol, caproic alcohol, caprylic alcohol, capric alcohol and undecyl alcohol, and technical-grade mixtures thereof, as are obtained, for example, in the hydrogenation of technical-grade fatty acid methyl esters or in the course of the hydrogenation of aldehydes from the Roelen oxosynthesis. Preference is given to alkyl oligoglucosides of chain length $C_8$-$C_{10}$ (DP=1 to 3), which are produced as forerunning in the distillative separation of technical-grade $C_8$-$C_{18}$-coconut fatty alcohol and can be contaminated with a fraction of less than 6% by weight of $C_{12}$-alcohol, and also alkyl oligoglucosides based on technical-grade $C_{9/11}$-oxo alcohols (DP=1 to 3). In addition, the alkyl and alkenyl radical R.sup.15 can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof, which can be obtained as described above. Preference is given to alkyl oligoglucosides based on hydrogenated $C_{12/14}$-coconut alcohol having a DP of from 1 to 3.
- sugar surfactants of the fatty acid N-alkylpolyhydroxyalkylamide type, a nonionic surfactant of the formula (E4-III), $$R^5CO\text{—}\underset{\underset{R^6}{|}}{N}\text{—}[Z] \qquad \text{(E4-III)}$$

in which $R^5CO$ is an aliphatic acyl radical having 6 to 22 carbon atoms, $R^6$ is hydrogen, an alkyl or hydroxyalkyl radical having 1 to 4 carbon atoms and [Z] is a linear or branched polyhydroxyalkyl radical having 3 to 12 carbon atoms and 3 to 10 hydroxyl groups. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. With regard to the method of preparation, reference may be made to the U.S. patent specifications U.S. Pat. No. 1,985,424, U.S. Pat. No. 2,016,962 and U.S. Pat. No. 2,703,798, and the international patent application WO 92/06984. An overview of this topic by H. Kelkenberg is given in Tens. Surf Det., Vol. 25, 8 (1988). The fatty acid N-alkylpolyhydroxyalkylamides are preferably derived from reducing sugars having 5 or 6 carbon atoms, in particular from glucose. The preferred fatty acid N-alkylpolyhydroxyalkylamides are therefore fatty acid N-alkylglucamides, as are given by the formula (E4-IV):

$$R^7CO\text{—}NR^8\text{—}CH_2\text{—}(CHOH)_4CH_2OH \qquad (E4\text{-}IV)$$

As fatty acid N-alkylpolyhydroxyalkylamides, preference is given to using glucamides of the formula (E4-IV) in which $R^8$ is hydrogen or an alkyl group and $R^7CO$ is the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachic acid, gadoleic acid, behenic acid or erucic acid or technical-grade mixtures thereof. Particular preference is given to fatty acid N-alkylglucamides of the formula (E4-IV) which are obtained by reductive amination of glucose with methylamine and subsequent acylation with lauric acid or C12/14-coconut fatty acid or a corresponding derivative. In addition, the polyhydroxyalkylamides can also be derived from maltose and palatinose.

Preferred nonionic surfactants have proven to be the alkylene oxide addition products onto saturated linear fatty alcohols and fatty acids having in each case 2 to 30 mol of ethylene oxide per mole of fatty alcohol or fatty acid. Preparations with excellent properties are likewise obtained if they comprise fatty acid esters of ethoxylated glycerol as nonionic surfactants.

These compounds are characterized by the following parameters. The alkyl radical R comprises 6 to 22 carbon atoms and can either be linear or branched. Preference is given to primary linear and 2-position methyl-branched aliphatic radicals. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. When using so-called oxo alcohols as starting materials, compounds with an uneven number of carbon atoms in the alkyl chain predominate.

In addition, the sugar surfactants may be present as nonionic surfactants in the compositions according to the invention. These can be present in the compositions according to the invention preferably in amounts of from 0.1 to 20% by weight, based on the particular overall composition. Amounts of from 0.5 to 15% by weight are particularly preferred, and very particular preference is given to amounts of from 0.5 to 7.5% by weight.

Compounds with alkyl groups used as surfactant may in each case be uniform substances. However, it is generally preferred when preparing the substances to start from native vegetable or animal raw materials, thus resulting in mixtures of substances with various alkyl chain lengths which depend on the particular raw material.

In the case of the surfactants which represent addition products of ethylene oxide and/or propylene oxide onto fatty alcohols or derivatives or these addition products, it is possible to use either products with a "normal" homolog distribution and also those with a narrowed homolog distribution. "Normal" homolog distribution is understood here as meaning mixtures of homologs which are obtained during the reaction of fatty alcohol and alkylene oxide using alkali metals, alkali metal hydroxides or alkali metal alkoxides as catalysts. Narrowed homolog distributions, by contrast, are obtained if, for example, hydrotalcites, alkaline earth metal salts of ether carboxylic acids, alkaline earth metal oxides, hydroxides and alkoxides are used as catalysts. The use of products with a narrowed homolog distribution may be preferred.

The surfactants are used in amounts of from 0.1 to 45% by weight, preferably 0.5 to 30% by weight and very particularly preferably from 0.5 to 25% by weight, based on the particular overall composition used according to the invention.

In a further embodiment, emulsifiers can be used in the compositions according to the invention. At the phase interface, emulsifiers bring about the formation of water-stable or oil-stable adsorption layers which protect the dispersed droplets against coalescence and thus stabilize the emulsion. Emulsifiers are therefore constructed like surfactants from a hydrophobic molecular moiety and a hydrophilic molecular moiety. Hydrophilic emulsifiers form preferably O/W emulsions and hydrophobic emulsifiers form preferably W/O emulsions. An emulsion is understood as meaning a droplet-like distribution (dispersion) of one liquid in another liquid with expenditure of energy to provide stabilizing phase interfaces by means of surfactants. The selection of these emulsifying surfactants or emulsifiers is governed by the substances to be dispersed and the particular external phase, and also the finely divided nature of the emulsion. Extensive definitions and properties of emulsifiers are given in "H. D. Dörfler, Grenzflächen-und Kolloidchemie [Interface and colloid chemistry], VCH Verlagsgesellschaft mbH. Weinheim, 1994". Emulsifiers which can be used according to the invention are, for example, addition products of from 4 to 100 mol of ethylene oxide and/or 0 to 5 mol of propylene oxide onto linear fatty alcohols having 8 to 22 carbon atoms, onto fatty acids having 12 to 22 carbon atoms and onto alkyl phenols having 8 to 15 carbon atoms in the alkyl group, $C_{12}$-$C_{22}$-fatty acid monoesters and diesters of addition products of from 1 to 30 mol of ethylene oxide onto polyols having 3 to 6 carbon atoms, in particular onto glycerol, ethylene oxide and polyglycerol addition products onto methyl glucoside fatty acid esters, fatty acid alkanolamides and fatty acid glucamides, $C_8$-$C_{22}$-alkyl mono- and oligoglycosides and ethoxylated analogs thereof, preference being given to degrees of oligomerization of from 1.1 to 5, in particular 1.2 to 2.0, and glucose as sugar component, mixtures of alkyl (oligo)glucosides and fatty alcohols, for example the commercially available product Montanov® 68, addition products of from 5 to 60 mol of ethylene oxide onto castor oil and hydrogenated castor oil, partial esters of polyols having 3-6 carbon atoms with saturated fatty acids having 8 to 22 carbon atoms, sterols. Sterols are understood as meaning a group of steroids which carry a hydroxyl group on carbon atom 3 of the steroid backbone and are isolated either from animal tissue (zoosterols) or from vegetable fats (phytosterols).

Examples of zoosterols are cholesterol and lanosterol. Examples of suitable phytosterols are ergosterol, stigmasterol and sitosterol. Sterols can also be isolated from fungi and yeast, the so-called mycosterols.

phospholipids. These are understood primarily as meaning the glucose phospholipids which are obtained, for example, as lecithins and phosphatidylcholines from e.g. egg yolk or plant seeds (e.g., soybeans).

fatty acid esters of sugars and sugar alcohols, such as sorbitol, polyglycerols and polyglycerol derivatives, such as, for example, polyglycerol poly-12-hydroxystearate (commercial product Dehymuls® PGPH), linear and branched fatty acids having 8 to 30 carbon atoms and the Na, K, ammonium, Ca, Mg and Zn salts thereof.

Compositions according to the invention comprise the emulsifiers preferably in amounts of from 0.1 to 25% by weight, in particular 0.1 to 3% by weight, based on the particular overall composition.

Preferably, compositions according to the invention can comprise at least one nonionogenic emulsifier with an HLB value of from 8 to 18, according to the definitions given in Römpp Lexikon Chemie [Römpp Chemistry Lexicon] (Ed. J. Falbe, M. Regitz), $10^{th}$ edition, Georg Thieme Verlag Stuttgart, N.Y., (1997), p. 1764. Nonionogenic emulsifiers with an HLB value of 10-15 may be particularly preferred according to the invention.

Compositions according to the invention preferably comprise at least one linear or branched, saturated or unsaturated fatty alcohol. Fatty alcohols which can be used are fatty alcohols with $C_6$-$C_{30}$, preferably $C_{10}$-$C_{22}$, and very particularly preferably $C_{12}$-$C_{22}$ carbon atoms. For the purposes of the invention, it is possible to use, for example, decanol, octanol, octenol, dodecanol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, the intention being for this list to be of exemplary and nonlimiting character. However, the fatty alcohols originate from preferably natural fatty acids, it usually being possible to start from a recovery from the esters of the fatty acids by reduction. According to the invention, it is likewise possible to use those fatty alcohol cuts which are produced by reduction of naturally occurring triglycerides, such as beef tallow, palm oil, peanut oil, rapeseed oil, cotton seed oil, soya oil, sunflower oil and linseed oil or fatty acid esters arising from their transesterification products with corresponding alcohols, and thus constitute a mixture of different fatty alcohols. Such substances are available commercially, for example, under the names Stenol®, e.g. Stenol® 1618 or Lanette®, e.g. Lanette® O or Lorol®, e.g. Lorol® C8, Lorol® C14, Lorol® C18, Loral® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. According to the invention, it is of course also possible to use wool wax alcohols, as are commercially available, for example, under the names Corona®, White Swan®, Coronet® or Fluilan®.

Fatty alcohols are used in amounts of from 0.1 to 20% by weight, based on the total preparation, preferably in amounts of from 0.1 to 10% by weight.

Compositions according to the invention can additionally comprise a viscosity-increasing compound, referred to below as thickener.

Thickeners which can be used according to the invention are, for example, agar agar, guar gum, alginates, xanthan gum, gum Arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, and viscosity-increasing polymers based on polyacrylate, as are sold, for example, under the trade names Pemulen®, Aculyn® and Carbopol®. Furthermore, a mixture of diesters of 1,2-propylene glycol with fatty acids, for example the thickener with the INCI name Propylene Glycol Dicaprylate/Dicaprate, is preferably used in the compositions according to the invention.

In addition, the following compounds may be present in the compositions according to the invention:

linear and/or branched fatty acids, preferably $C_2$-$C_{30}$-fatty acids, particularly preferably $C_4$-$C_{18}$ fatty acids, most preferably $C_6$-$C_{10}$-fatty acids and/or physiologically compatible salts thereof; further examples are formic acid, acetic acid, propionic acid, butyric acid, isobutyric acid, valeric acid, isovaleric acid, pivalic acid, oxalic acid, malonic acid, succinic acid, glutaric acid, lactic acid, glyceric acid, glyoxylic acid, adipic acid, pimellic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthalic acid, toluic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolcarboxylic acid, 1,2,4,6,7-naphthalenepentaacetic acid, malonaldehydic acid, 4-hydroxyphthalamidic acid, 1-pyrazolecarboxylic acid, gallic acid or propanetricarboxylic acid, polyhydroxy compounds; of particular mention here are
sugars with 5 and/or 6 carbon atoms, in particular as mono- and/or oligosaccharides, for example glucose, fructose, galactose, lactose, arabinose, ribose, xylose, lyxose, allose, altrose, mannose, gulose, idose, talose and sucrose and/or derivatives thereof, e.g. ether derivatives, amino derivatives and/or acetyl derivatives, such as acetylated glucose, e.g. tetraacetyl glucose, pentaacetyl glucose and/or 2-acetamido-2-desoxy glucose. Preferred sugar building blocks are glucose, fructose, galactose, allose, lactose, arabinose and sucrose; glucose, galactose and lactose are particularly preferred;

onic acids, in particular gluconic acid, glucuronic acid;
polyols, such as, for example, glucamines, glycerol, monoglycerides or diglycerides, 2-ethyl-1,3-hexanediol, 2-hydroxymethylpropanetriol, glycols, such as ethylene glycol, diethylene glycol, triethylene glycol, propylene glycol, dipropylene glycol, 1,3-butanediol;

polyhydroxy acids, such as, for example, pentahydroxyhexanoic acid, tetrahydroxypentanoic acid and/or derivatives thereof, such as, for example, ethers, esters and/or amides, e.g. pentahydroxyhexanamide and/or physiologically compatible salts thereof;

further examples: citric acid, malic acid or tartaric acid.
Pantolactone
panthenol and/or derivatives thereof;
further vitamins, such as, for example, vitamin B6, C and/or E and/or derivatives thereof;

hydroxy acids, such as, for example, α-, β-hydroxy fatty acids and keto fatty acids and/or physiologically compatible salts thereof; such as, for example, salicylic acid or lactic acid, glyoxylic acid, glycolic acid.

water-soluble polymers with a setting effect, e.g. polyvinylpyrrolidone, vinyl acetate/crotonic acid copolymers, antidandruff active ingredients, such as, for example, picrotone olamine, zinc omadine, active ingredients such as allantoin, pyrrolidonecarboxylic acids, plant extracts, pH regulators and buffers, such as, for example, citric acid/sodium citrate, ammonium carbonate, ammonium hydrogen carbonate, guanidine carbonate, ammonia, sodium hydroxide, complexing agents, such as EDTA, NTA, organophosphonic acids, dipicolinic acid photoprotective agents (UV absorbers)

oil, fat and wax components, preferably in emulsified form, dyes, opacifiers and pearlizing agents, and optionally aerosol propellant gases.

The invention secondly relates to a method of reshaping, in particular smoothing, keratin-containing fibers, in particular human hair, in which
(i) the fibers are shaped with the help of shaping aids after, before or during step (ii),
(ii) an aqueous composition comprising at least one keratin-reducing compound is applied to the fibers,
(iii) the fibers are rinsed and optionally dried after a contact time Z1,
(iv) then a composition of the first inventive subject-matter is applied to the fibers and rinsed out again after a contact time Z2.

Shaping aids for the purposes of the method according to the invention may be
e.g. rollers or curlers in the case of a permanent wave,
or aids for mechanical smoothing, such as a comb or a brush, a smoothing board or a heatable smoothing iron in the case of hair smoothing.

If the shaping aids, for example rollers, are attached to the fiber in the course of a permanent waving process for a prolonged period, then it is expedient to remove these shaping aids before step (iii) or after step (iv). In this connection, it may be advantageous to leave the shaping aids in the hair during step (iv), to remove them afterwards and then to repeat step (iv) as a so-called after-fixing step (v).

In a preferred embodiment of the invention, the keratin-containing fibers are wetted before step (i). This can occur by spraying the fibers with a liquid, preferably with water. Preferably, before step (i), the fibers are shampooed with a conventional shampoo, rinsed and then towel-dried. When towel-drying is complete, a perceptible residual moisture remains in the hair.

It is preferred, in the course of a hair smoothing, to smooth the fibers during the contact time Z1 from step (ii) mechanically, in particular by combing or using a smoothing board.

According to the invention, mechanical smoothing is understood as meaning a straightening of the frizzy fibers along their longest spatial dimension.

The contact time Z1 is preferably 5-60 minutes, particularly preferably 10-30 minutes. The contact time Z2 is preferably 1-30 minutes, particularly preferably 5-20 minutes.

For the purposes of the invention, an aqueous composition comprises at least 50% by weight of water, based on the weight of the total composition. This aqueous composition can be in various forms, for example in the form of a lotion, oil-in-water emulsion or water-in-oil emulsion.

The keratin-reducing compounds present in the aqueous composition of step (ii) are preferably selected from compounds with at least one thiol group, and derivatives thereof, from sulfites, hydrogensulfites and disulfites.

Compounds with at least one thiol group and derivatives thereof are, for example, thioglycolic acid, thiolactic acid, thiomalic acid, phenylthioglycolic acid, mercaptoethanesulfonic acid and salts and esters thereof (such as, for example, isooctyl thioglycolate and isopropyl thioglycolate), cysteamine, cystein, colored salts and salts of sulfurous acid. The monoethanolammonium salts or ammonium salts of thioglycolic acid and/or of thiolactic acid, and the free acids are preferably suitable. These are used in the aqueous composition preferably in concentrations of from 0.5 to 2.0 mol/kg at a pH of from 5 to 12, in particular from 7 to 9.5. To establish this pH, the aqueous compositions usually comprise alkalizing agents, such as ammonia, alkali metal and ammonium carbonates and hydrogencarbonates or organic amines, such as monoethanolamine.

Examples of keratin-reducing compounds of the disulfites which may be present in the aqueous composition are alkali metal disulfites, such as, for example, sodium disulfite ($Na_2S_2O_5$) and potassium disulfite ($K_2S_2O_5$), and magnesium disulfite and ammonium disulfite (($NH_4)_2S_2O_5$). Ammonium disulfite may be preferred here according to the invention. Examples of keratin-reducing compounds of the hydrogensulfites which may be present in the aqueous composition are hydrogensulfites as alkali metal, magnesium, ammonium or alkanolammonium salt based on a $C_2$-$C_4$-mono-, di- or trialkanolamine. Ammonium hydrogensulfite may here be a particularly preferred hydrogensulfite. Examples of keratin-reducing compounds of the sulfites which may be present in the aqueous composition are sulfites as alkali metal, ammonium or alkanolammonium salt based on a $C_2$-$C_4$-mono-, di- or trialkanolamine. Ammonium sulfite is preferred here. The pH of the aqueous composition when using sulfite and/or disulfite and/or hydrogensulfite is preferably adjusted to a value in the neutral range from pH 5 to 8, preferably from pH 6 to 7.5.

Preferred $C_2$-$C_4$-alkanolamines according to the invention are 2-aminoethanol(monoethanolamine) and N,N,N-tris(2-hydroxyethyl)amine(triethanolamine). Monoethanolamine is a particularly preferred $C_2$-$C_4$-alkanolamine, which is used in particular in an amount of from 0.2 to 6% by weight, based on the total aqueous composition.

The keratin-reducing compound is preferably used in an amount of from 5 to 20% by weight, based on the total aqueous composition.

Moreover, the aqueous composition can comprise further components which promote the effect of the keratin-reducing compound on the keratin. Such components are, for example, swelling agents for keratin-containing fibers, such as, for example, $C_1$-$C_6$-alcohols and water-soluble glycol or polyols, such as, for example, glycerol, 1,2-propylene glycol or sorbitol and urea or urea derivatives, such as, for example, allantoin and guanidine, and imidazole and derivatives thereof. A preferred further component is 1,2-propylene glycol, in particular in an amount of from 0.1 to 5% by weight. In each case, the quantitative data refers to the total aqueous composition. In a preferred embodiment, the aqueous composition comprises 0 to 5% by weight of 1,2-propylene glycol and/or 0 to 5% by weight of urea.

A dry keratin-containing fiber according to step (iii) of the method according to the invention is then present if the water residues adhering to the hair have evaporated sufficiently for the hairs to fall individually. Preferably, in the case of a dry keratin-containing fiber, either the moisture content of the fiber is essentially in equilibrium with the moisture in the air, or the fiber absorbs moisture from the ambient air. Such a dry fiber is preferably achieved by drying the wet fibers with hot air using a hair dryer. Drying in step (iii) is then preferably carried out if a heat treatment takes place between step (iii) and step (iv) in the course of a smoothing process during an additional smoothing step, e.g. with appropriately heated plates.

In a further embodiment, in the course of a hair smoothing, the fibers are subjected after step (iii) to a heat treatment with mechanical smoothing of the fibers at a temperature of 120-220° C. This thermal treatment with mechanical smoothing of the fibers preferably takes place at a temperature of 140-200° C. The heat treatment can take place with hot air. In this case, the fiber is heated during combing at precisely the point at which mechanical smoothing takes place. Moreover, it is particularly preferred for the heat treatment to take place in the style of smoothing using appropriately heated plates, in particular metal or ceramic plates, by pressing the plate onto the fiber to be smoothed and moving the plate pressed onto the fiber along the fiber. The plates can, if appropriate, be coated with heat-resistant materials. The keratin-containing fiber to be smoothed is particularly preferably pressed between two appropriately heated plates and both plates are moved simultaneously along the longest spatial expansion of the fiber. In this connection, it is again preferred for the two plates to be joined together, so that the two plates can be moved uniformly along the fiber. If the heat treatment is carried out on living hair, then the fiber is attached at one end (hair root). In this case, the plates are preferably moved uniformly from the hair root along the entire fiber. This movement results in a mechanical smoothing of the fibers. A suitable appliance for the heat treatment is, for example, the appliance "Ceramic Flat-Master" (sold by: Efalock, Germany).

In addition, the fibers can be treated with a standard commercial conditioner between step (iii) and (iv) and/or in the course of an after-treatment at the end of the method according to the invention.

The invention thirdly relates to the use of the compositions of the first inventive subject-matter for the fixing of reshaped, in particular smoothed, keratin-containing fibers, in particular human hair.

The invention fourthly relates to a kit-of-parts comprising
(a) a composition of the first inventive subject-matter,
(b) an aqueous composition comprising at least one keratin-reducing compound, where each of the compositions from (a) and (b) is packaged in a separate container and
(c) optionally
  (i) one or more safety materials for avoiding undesired contact between the preparations and the human body, preferably gloves and/or
  (ii) one or more treatment agents in the form of a conditioner.

The kit-of-parts according to the invention makes available the compositions for carrying out the method according to the invention of the second inventive subject-matter.

The examples below are intended to explain the subject-matter of the invention in more detail:

EXAMPLES

The fixing compositions as in Table 1 were prepared by a standard method. The compositions F1 to F4 are in accordance with the invention. The compositions V1 and V2 are not in accordance with the invention. In addition, a smoothing cream as in Table 2 was prepared by a known procedure.

TABLE 1

Fixing compositions

| Raw material | F1 [% by wt.] | F2 [% by wt.] | F3 [% by wt.] | F4 [% by wt.] | V1 [% by wt.] | V2 [% by wt.] |
|---|---|---|---|---|---|---|
| Cetearyl alcohol | 4.00 | 4.00 | 4.00 | 4.00 | 4.00 | 4.00 |
| Eumulgin ® B3[1] | 0.50 | 0.50 | 0.50 | 0.50 | 0.50 | 0.50 |
| Ammonia (25% strength aqueous solution) | 0.80 | 0.80 | 0.80 | 0.80 | 0.80 | 0.80 |
| Dipicolinic acid | 0.10 | 0.10 | 0.10 | 0.10 | 0.10 | 0.10 |
| Turpinal ® SL[2] | 1.70 | 1.70 | 1.70 | 1.70 | 1.70 | 1.70 |
| Rheocare ® CTH (E)[3] | 1.00 | 1.00 | 1.00 | 1.00 | — | 1.00 |
| Dehyquart ® A CA[4] | 2.00 | 1.00 | 1.00 | 2.00 | — | — |
| Merquat ® 100[5] | — | — | — | 1.00 | — | — |
| Dehyquart ® E[6] | 1.00 | — | 1.00 | 1.00 | — | — |
| Dehyquart ® L80[7] | — | 1.00 | — | — | — | — |
| Dow Corning ® 1403[8] | 1.00 | 1.00 | — | 1.00 | — | — |
| Hydrogen peroxide (50% strength aqueous solution) | 4.00 | 4.00 | 4.00 | 4.00 | 4.00 | 4.00 |
| Water | ad 100 | ad 100 | ad 100 | ad 100 | ad 100 | ad 100 |

[1] Cetylstearyl alcohol, ethoxylated with 30 units of ethylene oxide (INCI name: Ceteareth-30) (Cognis)
[2] 1-Hydroxyethane-1,1-diphosphonic acid (INCI name: Etidronic Acid, Aqua (Water)) (Solutia)
[3] Trimethylammonioethyl methacrylate chloride homopolymer (INCI name: Polyquaternium-37, Propylene Glycol Dicaprylate/Dicaprate, PPG-1 Trideceth-6) (CRL Cosmetic Rheologies, Ltd.)
[4] Trimethylhexadecylammonium chloride, 25% active substance (INCI name: Aqua (Water), Cetrimonium Chloride) (Cognis)
[5] Poly(dimethyldiallylammonium chloride) (INCI name: Polyquaternium-6) (Nalco)
[6] N-(2-Hydroxyhexadecyl)-N-2-hydroxyethyl-N,N-dimethylammonium chloride (23% active substance, INCI name: Aqua (Water), Hydroxycetyl Hydroxyethyl Dimonium Chloride) (Cognis)
[7] N,N-Di(cocoylethyl-N-hydroxyethyl-N-methylammonium methylsulfate (77% active substance; INCI name: Dicocoylethyl Hydroxyethylmonium Methosulfate, Propylene Glycol) (Cognis)
[8] INCI name: Dimethicone, Dimethiconol (Dow Corning)

TABLE 2

Smoothing cream

| Raw material | [% by wt.] |
|---|---|
| 1,2-Propylene glycol | 2.00 |
| Cetyl/stearyl alcohol | 9.00 |
| Lanette ® E[9] | 0.50 |
| Brij ® 35 P[10] | 0.50 |
| Natrosol ® 250 HR[11] | .025 |
| Ammonia (25% strength aqueous solution) | 5.00 |
| Turpinal ® SL[2] | 0.25 |
| Ammonium thioglycolate (71% strength aqueous solution) | 18.00 |
| Ammonium carbonate | 4.00 |
| Promois Silk ® 1000[12] | 1.00 |
| Dow Corning ® 1403[8] | 0.50 |
| Perfume | 1.00 |
| Water | Ad 100 |

[9]Sodium cetearyl sulfate (Cognis)
[10] Polyethylene glycol monolauryl ether with 23 units of ethylene oxide (INCI name: Laureth-23) (Uniqema)
[11]Hydroxyethylcellulose (Hercules)
[12]Collagen hydrolysate (INCI name: Hydrolyzed Silk) (RITA Corp.)

Experimental Procedure and Assessment of the Results

A group of test subjects was chosen, the members of which had comparatively tightly curled hair with an identical degree of damage prior to the start of the implementation of the smoothing process.

The entire head hair of a test subject was wetted with water and towel-dried.

The entire hair was treated with the above smoothing cream and combed smooth. After a contact time of 20 minutes, the hair was rinsed and carefully towel-dried. The hair was then treated with one of the fixing compositions as in Table 1 and combed smooth again. After a contact time of 15 minutes, the hair was rinsed with water and dried.

This procedure was carried out with all of the fixing compositions F1 to F4, V1 and V2 in Table 1. One test subject was required per fixing composition.

The smoothing result and the combability was assessed by six trained experts. These trained experts were informed which of the test subjects should be compared with one another. However, it was not revealed which of these test subjects was treated in accordance with the invention and which was not.

The valuation scale was:
++ much better than comparison test subject
+ better than comparison test subject
◇ exactly as comparison test subject
− poorer than comparison test subject
−− much poorer than comparison test subject The results obtained are given in Table 3.

TABLE 3

Evaluation

| | Tress treated with fixing composition F: | | | |
|---|---|---|---|---|
| | F1 | F2 | F3 | F4 |
| Smoothing result compared to V1 | ++ | ++ | ++ | ++ |
| Smoothing result compared to V2 | + | + | + | + |
| Combability compared to V1 | ++ | ++ | ++ | ++ |
| Combability compared to V2 | + | + | + | + |

We claim:

1. A method for the reshaping of keratin-containing fibers comprising:
   i. shaping the fibers with the help of shaping aids after, before or during step (ii),
   ii. applying an aqueous composition comprising at least one keratin-reducing compound is applied to the fibers,
   iii. rinsing and optionally drying the fibers after a contact time Z1,
   iv. applying to the smoothed fibers a composition comprising
      at least one oxidizing agent and
      an active ingredient combination of
      (a) a cationic polymer having at least one structural element according to general formula (I),

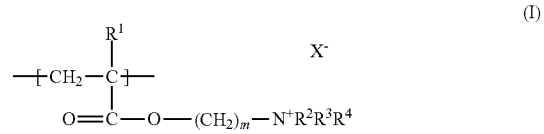

wherein
      $R^1$ is a $(C_1-C_4)$-alkyl group,
      $R^2$, $R^3$ and $R^4$, independently of one another, are $(C_1-C_4)$-alkyl groups,
      m is a number 1, 2, 3 or 4, and
      $X^-$ is a physiologically compatible organic or inorganic anion,
   (b) at least one quaternary ammonium compound according to formula (II)

$$(R^5)_y(Me)_{(4-y)}N^+Y^- \qquad (II)$$

wherein
      $R^5$ is a linear or branched $(C_8-C_{30})$-alkyl group,
      y is 1 or 2,
      $N^+$ is a nitrogen cation, and
      $Y^-$ is a physiologically compatible organic or inorganic anion, and
   (c) at least one quaternary ammonium compound having at least one group according to formula (III), $$R^6-A^1-A^2-A^3- \qquad (III)$$

wherein
      $R^6$ is a saturated or unsaturated, linear or branched, optionally substituted $(C_8-C_{30})$-hydrocarbon group,
      $A^1$ is a carbonyl group or a direct bond,
      $A^2$ is a direct bond, NH or an oxygen atom, and
      $A^3$ is a $(C_2-C_4)$-alkylene group or a $(C_2-C_4)$-hydroxyalkylene group,
      with the provisos that
      $A^3$ bonds to the quaternary nitrogen atom of the quaternary ammonium compound and $A^3$ is a $(C_2\text{-}C_4)$-hydroxyalkylene group when $A^1$ and $A^2$ are a direct bond, wherein the at least one quaternary ammonium compound according to formula (III) comprises N N-dimethyl-N-(2-hydroxyethyl)-N-(2-hydroxyhexadecyl)-ammonium chloride, wherein the quantitative ratio of components (a) to (c) is in the range from 1:1 to 3:1, and wherein the quantitative ratio of components (a) to (b) is in the range from 1.5:1 to 3:1, and v. rinsing the composition out after a contact time Z2.

2. The method according to claim 1, further comprising wetting the keratin-containing fibers before step (i).

3. The method according to claim 1, wherein the oxidizing agent is hydrogen peroxide.

4. The method according to claim 1, wherein the oxidizing agent is present in an amount of from 0.5 to 3.0% by weight, based on the weight of the composition.

5. The method according to claim 1, wherein the cationic polymer having at least one structural element according to formula (I) is a homopolymer of this structural element.

6. The method according to claim 1, wherein the polymer is present in an amount of from 0.01 to 10% by weight, based on total weight of the composition.

7. The method according to claim 1, wherein the compound according to formula (II) is chosen from salts of dicetyldimethylammonium, cetyltrimethylammonium, distearyldimethylammonium or stearyltrimethylammonium.

8. The method according to claim 1, wherein the quaternary ammonium compounds (c) are present in an amount of from 0.05 to 5% by weight, based on the weight of the composition.

9. The method according to claim 1, wherein the quaternary ammonium compounds (c) are chosen from quaternary ammonium compounds having one or two groups according to formula (III).

10. The method according to claim 1, wherein radical $R^6$ according to formula (III) is a linear or branched $(C_8\text{-}C_{30})$-alkyl group, linear or branched $(C_8\text{-}C_{30})$-alkenyl group, a hydroxy-$(C_8\text{-}C_{30})$-alkyl group or an oligohydroxy-$(C_8\text{-}C_{30})$-alkyl group.

11. The method according to claim 1, wherein the group according to formula (III) is chosen from an ω-[$(C_8\text{-}C_{30})$-alkanoyloxy]-$(C_2\text{-}C_4)$-alkyl group, an ω-[$(C_8\text{-}C_{30})$-alkylamido]-$(C_2\text{-}C_4)$-alkyl group, or a $(C_{10}\text{-}C_{36})$-hydroxyalkyl group.

12. The method according to claim 1, wherein the quaternary ammonium compound (c) is chosen from compounds according to formula (c1)

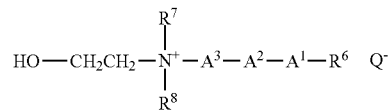

(c1)

wherein
$R^7$ and $R^8$, independently of one another, are a hydrogen atom, a $(C_2\text{-}C_{30})$-acyl group or a linear or branched $(C_1\text{-}C_{30})$-alkyl group,
$R^6$ is a linear or branched $(C_8\text{-}C_{30})$-alkyl group or a linear or branched $(C_8\text{-}C_{30})$-alkenyl group,
$A^1$ is a direct bond or a carbonyl group,
$A^2$ is a direct bond, a group NH or an oxygen atom,
$A^3$ is a $(C_2\text{-}C_4)$-alkylene group or a $(C_2\text{-}C_4)$-hydroxyalkylene group, and
$Q^-$ is a physiologically compatible organic or inorganic anion,
with the proviso that $A^3$ is a $(C_2\text{-}C_4)$-hydroxyalkylene group if $A^1$ and $A^2$ are a direct bond.

13. The method according to claim 1, wherein the quaternary ammonium compound (c) is chosen from compounds according to formula (c2)

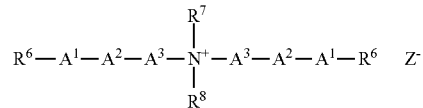

(c2)

wherein
$R^7$ and $R^8$, independently of one another, are a hydrogen atom, a $(C_1\text{-}C_4)$-alkyl group or $(C_2\text{-}C_4)$-hydroxyalkyl group,
$R^6$ is a linear or branched $(C_8\text{-}C_{30})$-alkyl group, linear or branched $(C_8\text{-}C_{30})$-alkenyl group, a hydroxy-$(C_8\text{-}C_{30})$alkyl group or an oligohydroxy-$(C_8\text{-}C_{30})$-alkyl group,
$A^1$ is a carbonyl group,
$A^2$ is a group NH or an oxygen atom,
$A^3$ is a $(C_2\text{-}C_4)$-alkylene group, a $(C_2\text{-}C_4)$-hydroxyalkylene group, and
$Z^-$ is a physiologically compatible organic or inorganic anion.

14. The method according to claim 1, wherein the composition further comprises at least one silicone.

15. The method according to claim 1, wherein step (iii) comprises rinsing and drying the fibers after the contact time Z1.

16. The method according to claim 1, wherein the composition further comprises diesters of propylene glycol with a mixture of caprylic acid, capric acid, and tridecyl polyoxypropylene polyoxyethylene ether.

* * * * *